United States Patent [19]

Doyle

[11] Patent Number: 5,218,856
[45] Date of Patent: Jun. 15, 1993

[54] ANALYSIS OF LIQUID-CARRIED IMPURITIES BY MEANS OF SPARGING

[75] Inventor: Walter M. Doyle, Laguna Beach, Calif.

[73] Assignee: Axiom Analytical, Inc., Irvine, Calif.

[21] Appl. No.: 922,754

[22] Filed: Jul. 30, 1992

Related U.S. Application Data

[63] Continuation-in-part of Ser. No. 846,859, Mar. 6, 1992, abandoned.

[51] Int. Cl.$^5$ ............................................. G01N 33/18
[52] U.S. Cl. ..................................... 73/19.1; 73/61.41
[58] Field of Search .................... 73/19.1, 19.01, 64.45, 73/61.41

[56] References Cited

U.S. PATENT DOCUMENTS

| | | | |
|---|---|---|---|
| 2,722,826 | 11/1955 | Milligan et al. | 73/64.45 |
| 3,150,516 | 9/1964 | Linnenbom et al. | 73/19.1 |
| 3,800,595 | 4/1974 | Vincent | 73/19.1 |
| 4,154,086 | 5/1979 | Button et al. | 73/19.02 X |
| 4,330,385 | 5/1982 | Arthur et al. | 73/19.1 X |
| 4,745,795 | 5/1988 | Emmert | 73/61.41 X |
| 5,127,259 | 7/1992 | Kahl et al. | 73/19.1 |
| 5,147,561 | 9/1992 | Burge et al. | 73/19.1 X |

FOREIGN PATENT DOCUMENTS 314938 12/1989 Japan ................................. 73/19.1

*Primary Examiner*—Tom Noland
*Assistant Examiner*—Joseph W. Roskos
*Attorney, Agent, or Firm*—Thomas J. Plante

[57] ABSTRACT

A method for determining the concentration of individual solutes in a body of liquid, e.g., measuring contaminants in waste water. A sparging IR process is used, in which gas in the form of minute bubbles moves upwardly in a non-flowing body of liquid. The gas remove vaporized samples of the subject solutes and flows to a gas cell, where it is subjected to infrared spectrometer analysis. The true concentration of each subject solute is measured by plotting its concentration values against elapsed time, and then extrapolating back to time zero to determine the initial concentration of the solute. In addition, the rate of depletion is used to determine the ratio of vapor pressure to solubility of the solute. Replotting the original data using logarithm values can simplify the extrapolation.

27 Claims, 10 Drawing Sheets

ANALYSIS OF LIQUID-CARRIED IMPURITIES BY MEANS OF SPARGING

This application is a continuation-in-part of application Ser. No. 07/846,859, filed Mar. 6, 1992, now abandoned.

BACKGROUND OF THE INVENTION

This invention relates to a process and apparatus for measuring substances in a body of liquid, e.g., contaminants in waste water discharged from chemical manufacturing plants. The present process is referred to as sparging, because gas bubbles are used to remove vaporized contaminant samples from the liquid. In systems of the type disclosed, the materials removed from the liquid are subjected to analysis by an instrument capable of measuring the concentration of specific chemicals in the gas phase as a function of time. This instrument could be in infrared spectrometer used in conjunction with a gas cell or a mass spectrometer.

Application Ser. No. 662,933, filed Mar. 1, 1991, having the same assignee as the present application, discusses in detail the purposes and functions of a novel sparging IR system, and refers to a prior sparging IR system developed by the duPont Corporation.

A deficiency in both of the sparging IR systems disclosed in the previous application is the possible inability to correctly measure the concentrations of some contaminants. The problem is due to depletion of constituent traces before their respective vapor pressures have reached equilibrium with the concentrations of the corresponding solutes in the waste water. This will lead to an unduly low measurement of any constituents which have been significantly depleted before the IR analysis occurs.

In application Ser. No. 662,933 this problem was recognized, as indicated by this quotation: "A further aspect of the present invention is the use of increased liquid flow rates to prevent or reduce depletion of contaminants which are only slightly soluble, and are therefore likely to be inaccurately measured, if they are significantly depleted during the sparging process. Having a sufficiently high ratio of liquid flow rate to gas flow rate is useful in preventing contaminant depletion."

Experience has shown that two of the values which control the contaminant concentration measurements vary considerably with operating conditions. One such value is the equilibrium vapor pressure (designated "$P_o$") of the pure substance being measured. The other such value is the solubility in water (designated "S") of the substance being measured. The value $P_o$ is temperature dependent, and the value S is both (a) highly temperature dependent, and (b) influenced by the presence of other chemicals in the water.

SUMMARY OF THE INVENTION

The present invention, in a sense, reverses the concepts of the prior sparging IR systems. Instead of trying to avoid depletion of the solute being measured, it subjects the solute to controlled depletion, in such a way as to plot the time history of its depletion.

From this time history of depletion, the solubility-to-vapor pressure ratio of the contaminant substance can be determined. And from that data the concentration of the contaminant at time zero can be readily established. This involves creation of a time depletion curve, which can be extrapolated back to time zero.

This depletion rate analysis eliminates the dependence of the concentration measurement on the solubility and inherent vapor pressure of the solute. Therefore, the temperature and the presence of additional solutes do not affect the measurement.

The discussion below will be primarily concerned with the use of the present invention in conjunction with infrared spectroscopy. However, it can be employed with any analytical measuring technique capable of measuring the concentrations of specific gasses as a function of time.

DETAILED DESCRIPTION OF THE PREFERRED PROCESS

Figure 1:
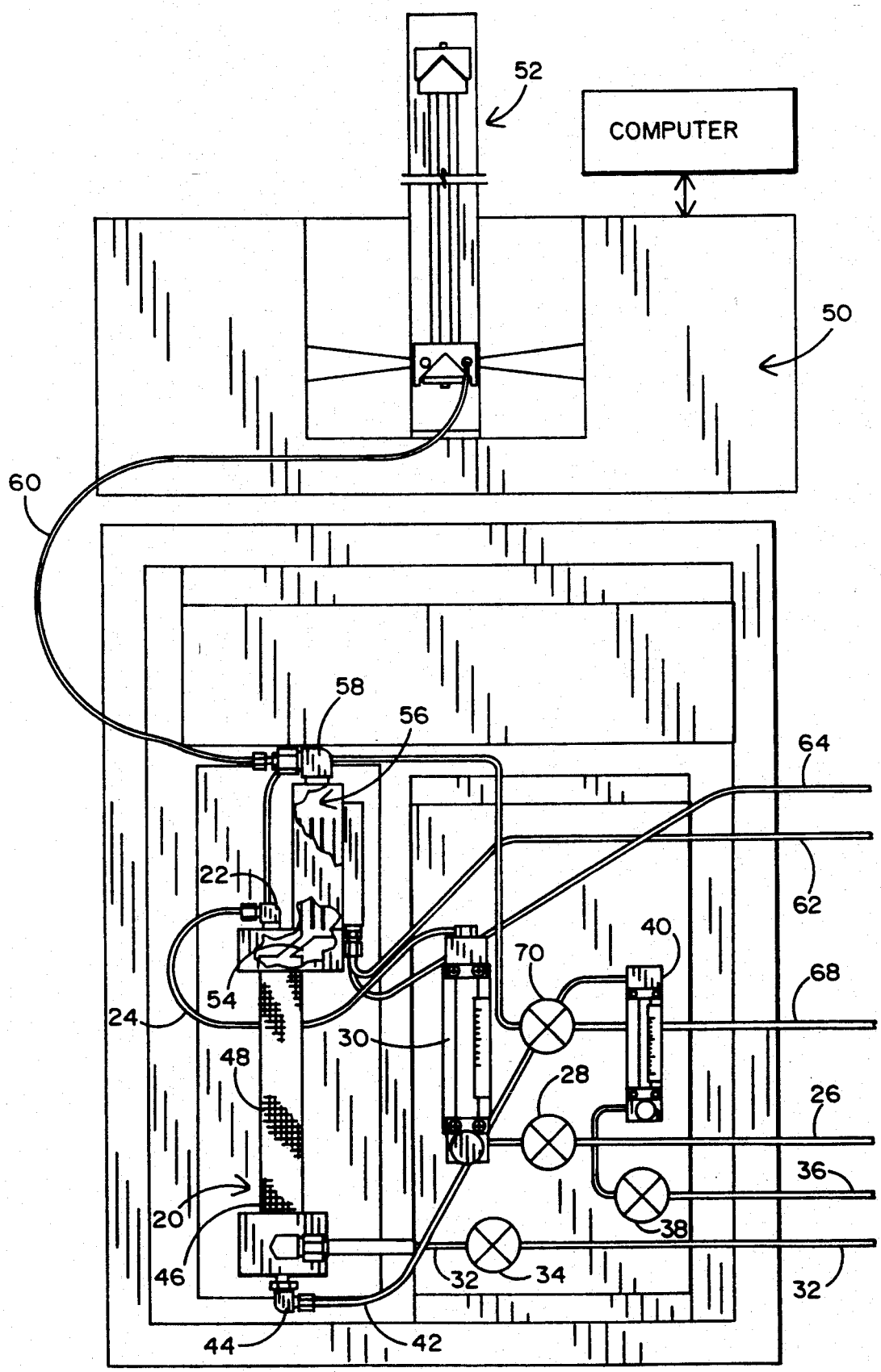
FIG. 1 is a schematic showing apparatus components which can be used in performing the novel method.

FIG. 1 shows diagrammatically (in a vertical plane) an apparatus which can be used to perform the novel process of this invention. Other combinations of components could be used, if desired.

FIG. 1 shows a sparging vessel 20, which contains the waste liquid (usually water). Liquid enters vessel 20 through a fitting 22 at the top of the vessel, from an input pipe 24. Starting at the right side of the figure, a water input pipe 26 leads to a flow control valve 28, after which the water passes through a velocity gauge 30, on its way to pipe 24. When water exits the sparging vessel 20, it flows through a drain pipe 32, passing through a flow control valve 34.

The air (or other gas), which creates the sparging effect by causing bubbles to rise inside the sparging vessel, enters through a pipe 36 (right side of drawing), passes through a flow control valve 38, a velocity gauge 40, and then pipe 42; and enters the bottom of the sparging vessel via a fitting 44.

The sparging bubbles are emitted into the water in the vessel 20 by a short, vertically-extending nozzle 46, which has a very large number of tiny holes for emitting air. The air moving through these holes forms bubbles, shown at 48, which rise through the water in the vessel. The bubbles combine with vaporized contaminants in the water to provide a suitable gas for analysis in a gas cell, which is part of an infrared spectrometer.

The infrared spectrometer is shown generally at 50. The gas cell, shown at 52, may incorporate, for example, the structural concepts described in common assignee U.S. Pat. No. 5,065,025. By means of interferometric analysis of the gas flowing in gas cell 52, the constituents in the gas are identified and measured.

The bubbles in the waste water provide a large air-liquid surface area for passage of dissolved volatile material (contaminants) into the gas phase of the analytical system. In the waste water, the contaminants to be measured are in liquid form. The sparging system is intended to reach equilibrium of the liquid and gas phases of the respective contaminants. Once such equilibrium is attained, measurement of the contaminant gases in the gas cell permits measurement of the liquid contaminants in the waste water flow.

According to basic principles relating to vapor pressure and changes of state between liquid and gas, a liquid in a closed container will evaporate until equilibrium vapor pressure is attained. At equilibrium, the rate of condensation of gas molecules equals the rate of vaporization of liquid molecules; and an equilibrium vapor pressure has been established. This equilibrium vapor pressure increases significantly with temperature increases; and it also increases with increased volatility of the liquid.

The contaminant materials in waste water from chemical processes generally have higher volatility than water. Such contaminants would eventually reach equilibrium vapor pressure by evaporation. However, excessive time would be required. Sparging tremendously increases the surface area of liquid to gas contact. The increase is many orders of magnitude, so that the gas-liquid equilibrium can be reached in a matter of seconds.

The gas which carries the contaminants leaves the sparging vessel via a short pipe 54, which connects to the bottom of a condenser 56. Gas passes from the top of condenser 56 at a fitting 58, and flows to the gas cell 52 via a pipe 60. The desired temperature in condenser 56 is maintained by controlling the flow of cooling water in inlet and outlet pipes 62 and 64.

The reasons for the condenser are discussed at length in common assignee application Ser. No. 07/662,933. Briefly, the purpose of the condenser is to maintain a precise water vapor pressure in the gas cell, so that the number of water vapor molecules per unit of gas volume in the gas cell is a fixed amount, which can be used in software calculations to remove the water vapor effect from the spectra produced by the gas cell (and the spectrometer system which includes the gas cell). This maintenance of a known (and therefore, subtractable) water vapor factor in the gas being analyzed can be accomplished by having condenser 24 maintain a precise temperature a few degrees above freezing.

FIG. 1 also shows a reference water connection. A pipe 68 and control valve 70 can be used to bring non-contaminated water occasionally into the vessel 20, when no contaminated water is present, for the purpose of obtaining background spectra.

The substance of the present invention is a novel process which obtains the desired data re amounts of contaminants. The present process functions with a static body of water in the vessel. Gas is sparged through a non-flowing volume of water for the purpose of determining both the initial concentration and the depletion rate for each contaminant.

The ultimate goal of the sparging IR system is to determine the concentration of each contaminant in the water stream. The relationship between liquid phase concentration and vapor pressure of each contaminant can be represented by either of these equations:

$$C = P S/P_o \text{ or } P = C P_o/S \tag{I-1}$$

where P is the vapor pressure of a given substance in the air stream, $P_o$ is the equilibrium vapor pressure of the pure substance, C is the concentration of the substance in the water stream, and S is the solubility of the substance in water. If $P_o$ and S are known, the concentrations of the various pollutants can be determined from the measured vapor pressures. In what follows, the letter "K" will be used to represent the ratio of these two factors, i.e., $K = P_o/S$.

"K" is the function which determines the partitioning of the solute between the vapor and liquid phases. For the volatile, weakly soluble substances of greatest environmental concern, K can have values three to four orders of magnitude greater than for water.

To make the infrared vapor phase measurement, it is first necessary to calibrate the system for the set of solute species likely to be present. This can be done by using one of several available multivariate quantitation approaches. The method most commonly used in the mid-IR spectral region is the "P" matrix approach.

In the "P" matrix method, the concentrations of the various species are expressed as a set of simultaneous equations involving measured absorbances in selected wavelength regions. This set of equations can be expressed in matrix form as $$C_G = PA \tag{I-2}$$

where $C_G$ is the set of gas phase molar concentrations, A is the set of measured IR absorbances, and P is the calibration "P" matrix.

The set of coefficients (matrix elements) which make up the "P" matrix are determined by calibrating the system using a set of samples having known concentrations.

Infrared quantitative analysis provides a measure of vapor phase concentrations. However, it is vapor pressure rather than vapor phase concentration that is directly related to liquid phase concentration. Therefore, the ideal gas law must be used:

$$P = C_G RT \tag{I-3}$$

where $C_G = n/V$. Here, R is the universal gas constant, n is the number of moles of vapor in the gas cell, V is the volume of the gas cell, and T is the gas temperature.

By combining Equation I-3 and Equation I-1, an expression is obtained for liquid concentration in terms of the measured vapor phase concentration:

$$C = P/K = C_G RT/K \tag{I-4}$$

where again, K is the partitioning function.

Thus, once the vapor phase concentration of a species is determined, all that is required to determine the liquid phase concentration is a knowledge of the temperature of the vapor in the gas cell and the value of the partitioning function, K, which is determined by the ratio $P_o/S$.

A problem that arises is that $P_o$ and S may not be known and, in fact, may vary considerably with operating conditions. Vapor pressure is highly temperature dependent. Solubility is temperature dependent and is influenced by the presence of other chemicals in the water. Thus, it is desirable to have a method for measuring these parameters, or at least their ratio, for the actual conditions which occur during the sparging process.

The method disclosed herein determines both CO and K during the same measurement, by studying the time dependence of the measured gas concentration while sparging a fixed volume of water. To understand how this can be done, first consider the simplified case of a single solute, constant temperature, and a small air volume. In this case, it can be shown that the dependence of concentration on time is a simple exponential, $$C_G(t) = C_G(O)2^{-\alpha t} \qquad (I\text{-}5)$$

where $\alpha$ can be called a depletion rate constant.

The measurement of two or more points on the depletion curve allows one to determine both the initial vapor phase concentration $C_G(O)$ and the value of $\alpha$.

The reciprocal of the depletion rate constant is the depletion half life, i.e., $$C_G(t) = C_G(O)/2, \text{ then } t = 1/\alpha \qquad (I\text{-}6)$$

The logarithm of the time dependence will be a straight line:

$$\log_2 C_G(t) = \log_2 C_G(O) - \alpha \qquad (I\text{-}7)$$

Figure 2:
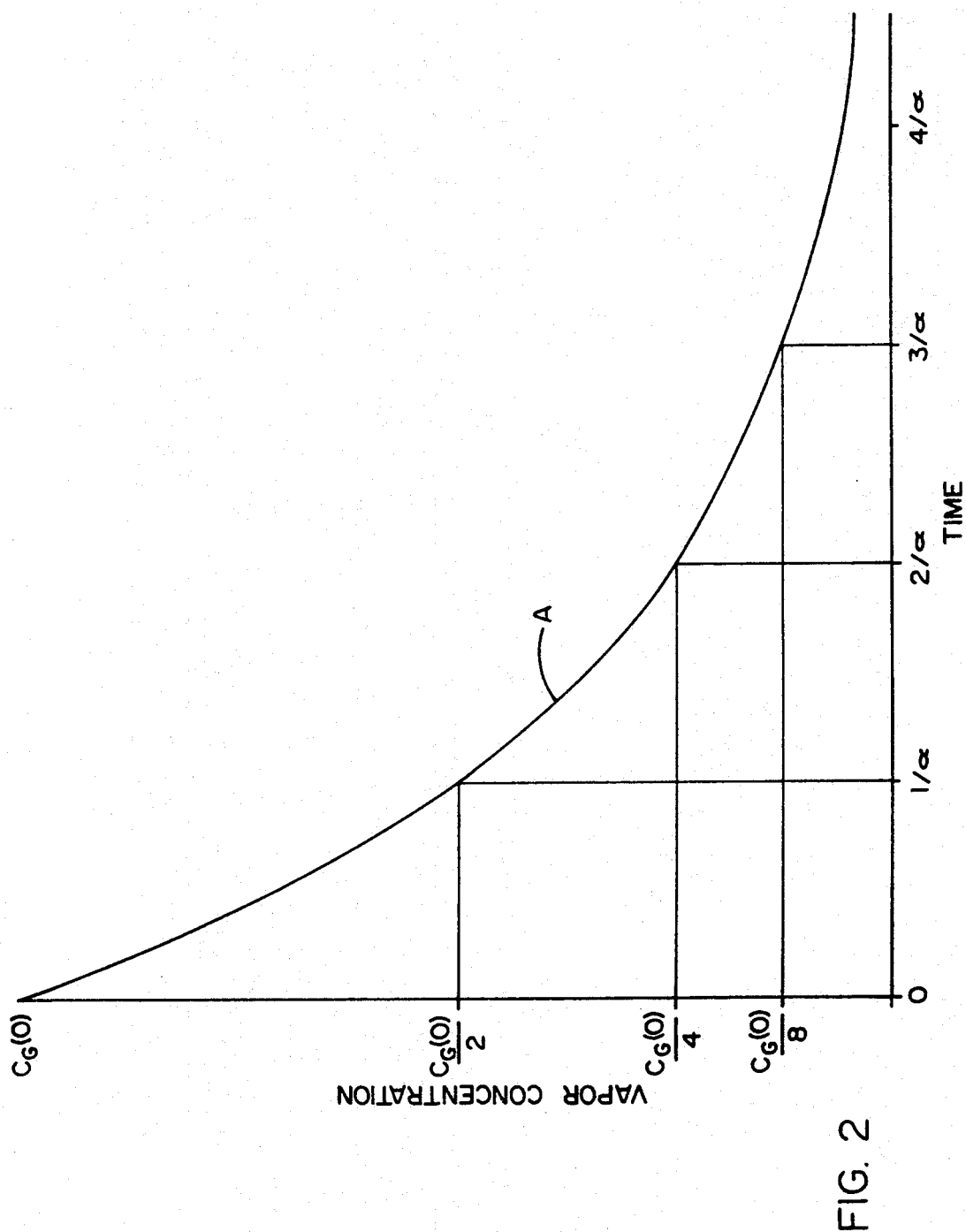
FIG. 2 is a graph showing a curve which plots theoretical vapor concentration of a subject solute against elapsed time.
Figure 3:
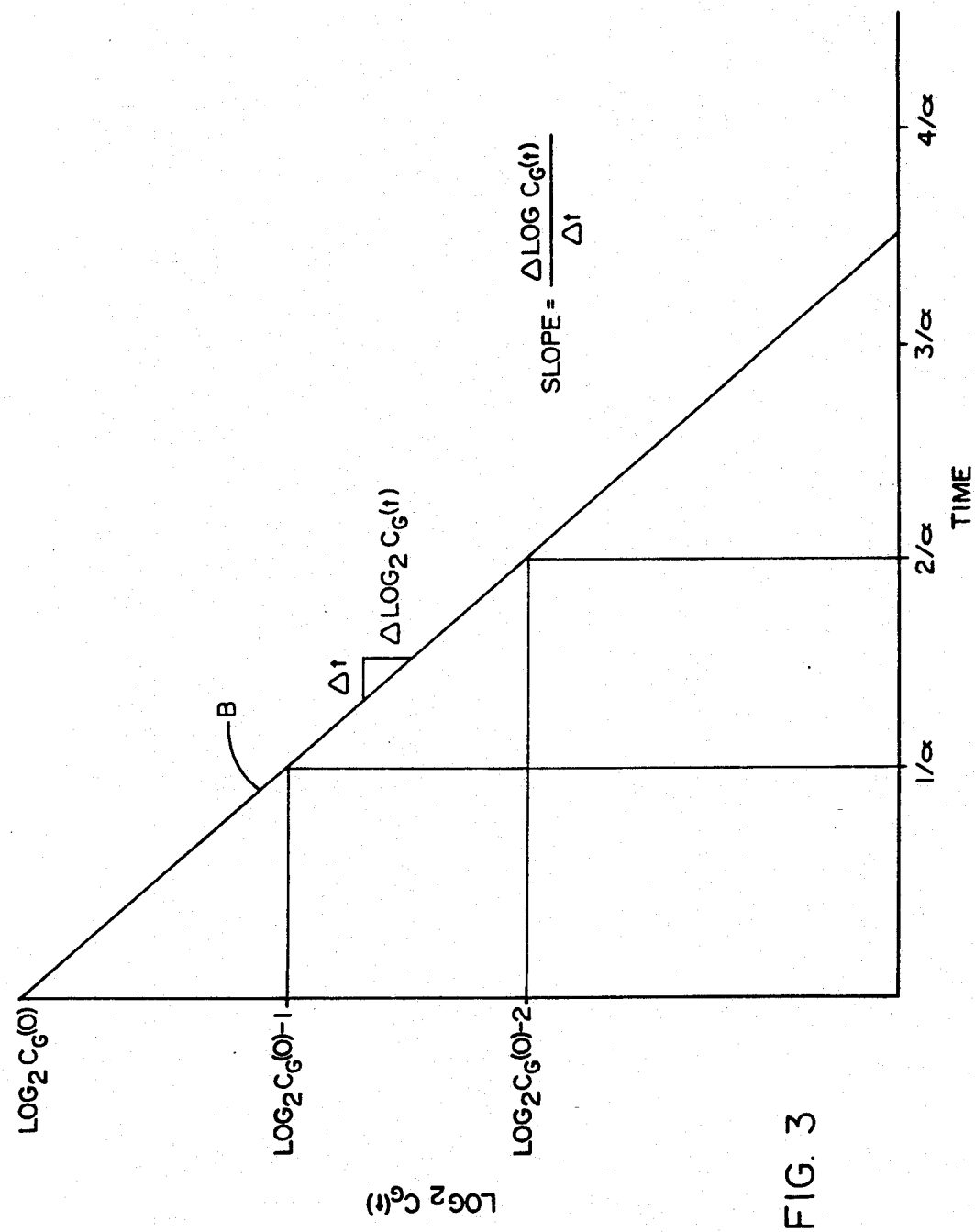
FIG. 3 is a graph based on FIG. 2, in which the data has been converted to logarithm values in order to obtain a straight-line slope.

FIGS. 2 and 3 illustrate the relationships just discussed. In both figures, time-related values are distributed along the X-axis, and vapor concentration-related values are distributed along the Y-axis. FIG. 2 has a curve, A, illustrating equation (I-1). The X-axis values are $1/\alpha$, $2/\alpha$, $3/\alpha$ and $4/\alpha$. At the top of the Y-axis, the curve represents the concentration of the substance before any depletion has occurred, i.e., at time zero. When the elapsed time reaches the value represented by $1/\alpha$, the concentration will have dropped to one-half of its initial (time zero) value. At time $2/\alpha$, the concentration will be one-fourth of its initial value; and at time $3/\alpha$, the concentration will be one-eighth of its initial value.

FIG. 3 has a straight-line slope B in which the concentration data of FIG. 2 is presented as the logarithmic equivalent, thus converting the curve A into a straight-line slope B. The logarithmic values simplify the determination of the vapor concentration value at time zero, $C_G(O)$.

The starting concentration, before the onset of depletion, has been determined by measuring the concentration at any two later times and then extrapolating back to time zero. This fact can be quite useful for the open loop measurement of solutes having low solubilities and hence fast depletion times.

As stated above, the measured value of $C_G(O)$ can be related to concentration of the solute in the water, if the value of the partitioning function, K, is known. By analyzing the time dependence of the depletion process, the inventor has discovered that this function (for a given solute) is directly proportional to the depletion rate constant $\alpha$. To understand this, introduce the concept of a half depletion volume, $V_h$. This is the volume of sparging air required to remove half of a given solute from the volume of air.

It will be demonstrated below that $$V_h = V_w RT/W_m K \qquad (I\text{-}8)$$

where $V_w$ = water volume, R = 0.08206, a universal constant, T = temperature at degrees Kelvin, and $W_m$ = molecular weight. For a fixed flow rate, f, the volume of air flowing through the vessel in time "t" will be equal to V = ft. Therefore, the half depletion volume of air will pass through the sparging vessel in a time, $t_h$, given by:

$$t_h = V_h/f \qquad (I\text{-}9)$$

Since this is identical to the half life defined above:

$$\alpha = 1/t_h = f/V_h \qquad (I\text{-}10)$$

or $$\alpha = (f/V_w)(W_m/RT)K \qquad (I\text{-}11)$$

Inverting this equation gives the desired expression:

$$K = \alpha(V_w/f)(RT/W_m) \qquad (I\text{-}12)$$

Since $\alpha$ is the slope of the log plot discussed above, it can easily be determined by measuring the vapor concentration in the gas stream at two or more times. Each of the other factors in the above equation is either a known constant or can be easily measured during the experiment. Thus, there is a basis for determining both the partitioning function, K, and the starting vapor concentration, $C_G(O)$ by the same experiment. Knowledge of the partitioning function enables the experimenter to determine the initial concentration of the solute in the water, based on the measured initial vapor concentration. By combining Equations I-4 and I-12, this equation results $$C(O) = (C_G(O)/\alpha)(fW_m/V_w) \qquad (I\text{-}13)$$

The significance of this method is that it enables one to measure C(O) independent of $P_o$ and S, and hence to eliminate the dependence of the measurement on such factors as temperature and the presence of additional solutes in the water sample.

The method can be further understood if it is recognized that the factor $C_G(O)/\alpha$ in equation I-13 is equal to the area under the depletion curve—i.e., for a simple exponential, the area is equal to:

$$I = \int_0^\infty C_G(t)dt = C_G(0)\int_0^\infty 2^{-\alpha t}dt$$

$$= C_G(0) \cdot \frac{2^{-\alpha t}}{-\alpha}\bigg|_0^\infty = C_G(0)[0 - 1/-\alpha] = C_G(0)/\alpha$$

For the more general case, in which the depletion curve is not a pure exponential, it can be shown that the initial liquid concentration is still given by $$C_G(O) = I(fW_m V_w)$$

where $$I = \int_0^\infty C_G(t)dt.$$

Thus, the starting liquid concentration can always be determined by integrating the area under the gas concentration depletion curve. However, the method is most useful when the form of the depletion curve is known (such as when it is a pure exponential). In this case, it is only necessary to measure enough points to fit the known function to the data. This makes it possible to make the measurement much more rapidly than would be the case if it were necessary to integrate the whole depletion curve.

A more detailed consideration of the foregoing assumptions requires discussion of the number of solutes, the temperature, and the air volume.

Figure 4:
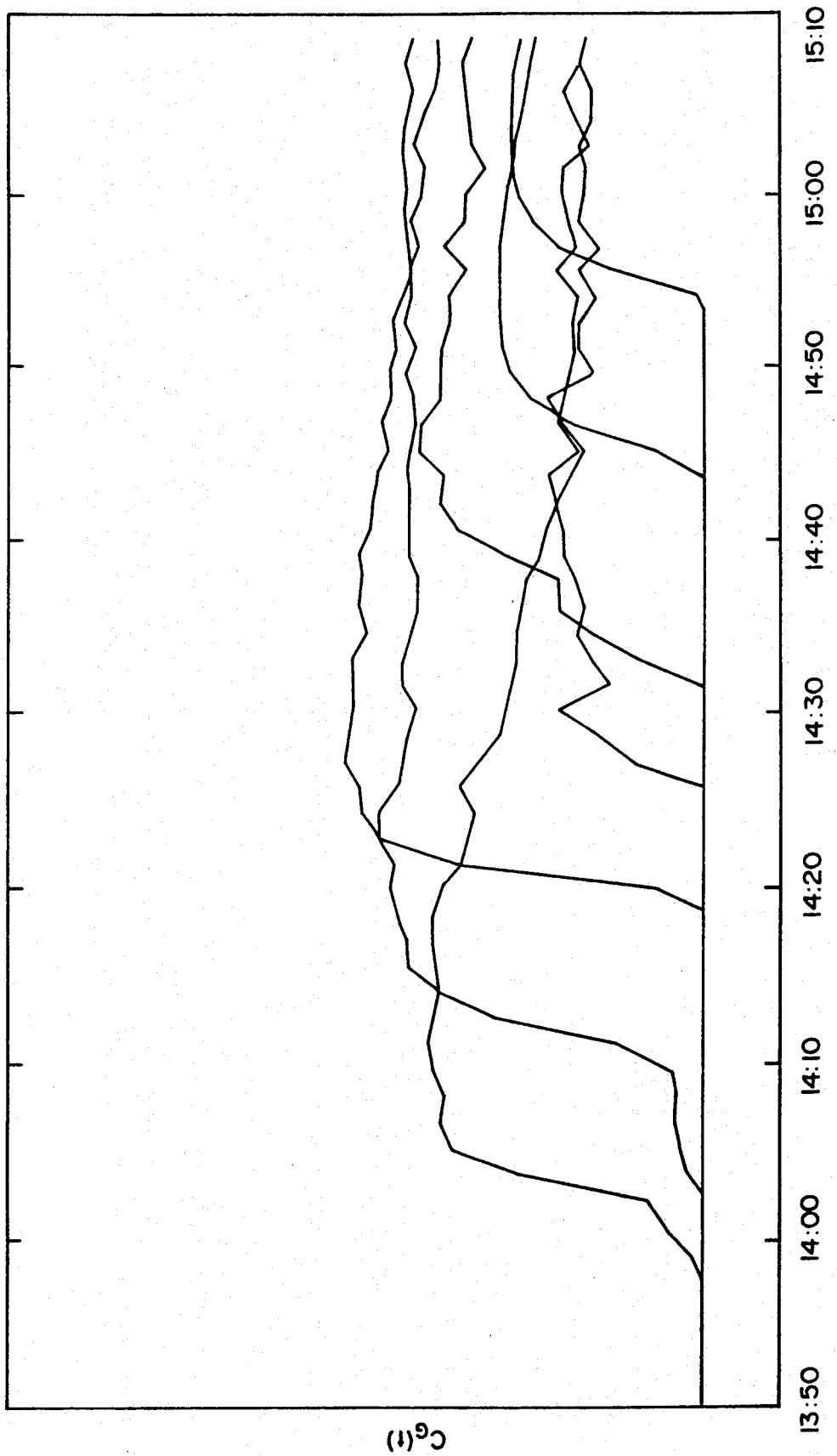
FIG. 4 is a graph showing seven curves which plot the measured concentration values of seven solutes against elapsed time.

The solubility of one solute in water can be influenced by the presence of a second solute. First, assume that both solutes have low solubility. Of necessity, both will be present in very low concentrations, and negligible interaction is expected between the two substances, since each solute molecule would be surrounded almost entirely by water molecules, and would thus have a very low probability of interacting with a molecule of the other solute. This prediction is supported by experiments in which up to seven different solutes were sequentially injected into a volume of water during closed loop sparging. As each new solute was injected, there was no measurable change in the measured concentrations of the solutes already present. FIG. 4 shows the results of the seven solute experiment.

A different situation would occur in the presence of a relatively high concentration of a highly soluble substance, such as methanol. In this case, the solubility of a weakly soluble substance would be affected by the presence of the interfering second substance. However, this situation does not present a problem. Since the second substance is highly soluble, its concentration will change relatively slowly during the sparging process. For many combinations of substances, the change in concentration of the interfering substance will be negligible during the time required to determine the decay rate constant for the solute of interest. Thus the value of K measured during this process will be valid and usable, although different from the value that would be obtained if the second substance were not present.

A third situation occurs when both the substance to be measure and the interfering substance have relatively high solubilities. This case is the least likely to be of interest, since the substances that are of greatest environmental concern have low solubilities. However, even this third case will often be amenable to analysis by more sophisticated mathematical methods, provided the identity of the interfering substance is known. The only cases that may turn out to be intractable are those in which both substances have quite similar depletion half lives. And even here, it may be possible to carry out the analysis by studying the interaction of the two substances in an independent set of experiments, and using the results to set up appropriate calibration.

Since the method disclosed herein uses a static sample of waste water, there is no concern about changes in the temperature of the incoming water stream during the measurement. However, it is possible for the water temperature to be changed by the sparging air, due to two factors, (1) the temperature of the air itself and (2) the cooling effect of evaporation. The effect of the first factor can be minimized by making certain that the temperature of the air is not substantially different from that of the water. The largest contributor to evaporative cooling will usually be the water itself, since the solute concentrations will usually be too low to materially affect the water temperature. And water evaporation is a relatively slow process, compared to the depletion rates of most of the pollutants of interest. Thus, for most measurements, the water temperature will not change significantly during the measurement. However, if this problem does occur, it is always possible to measure the water temperature and to perform a calibration of the temperature dependence of the solubility of the individual solutes.

If the depletion half volume of a given solute is comparable to or less than the volume of the air in the sparging vessel, the transfer lines, and the gas cell, the concentration will have started to decrease before the first measurement can be taken. An apparatus used to implement the method should therefore be capable of operating with a high ratio of water volume to air volume. This suggests the use of a tall, narrow sparging vessel, so as to minimize the head space at the top of the vessel for a given water volume. It also suggests the use of small transfer lines and the smallest practical gas cell.

Even with the above precautions, there will probably be some solutes for which the depletion time is comparable to the measurement time. However, as will be shown below, the measured decay will still be a simple exponential, and it will still be possible to extrapolate back to time zero to determine the starting concentration.

Figure 5:
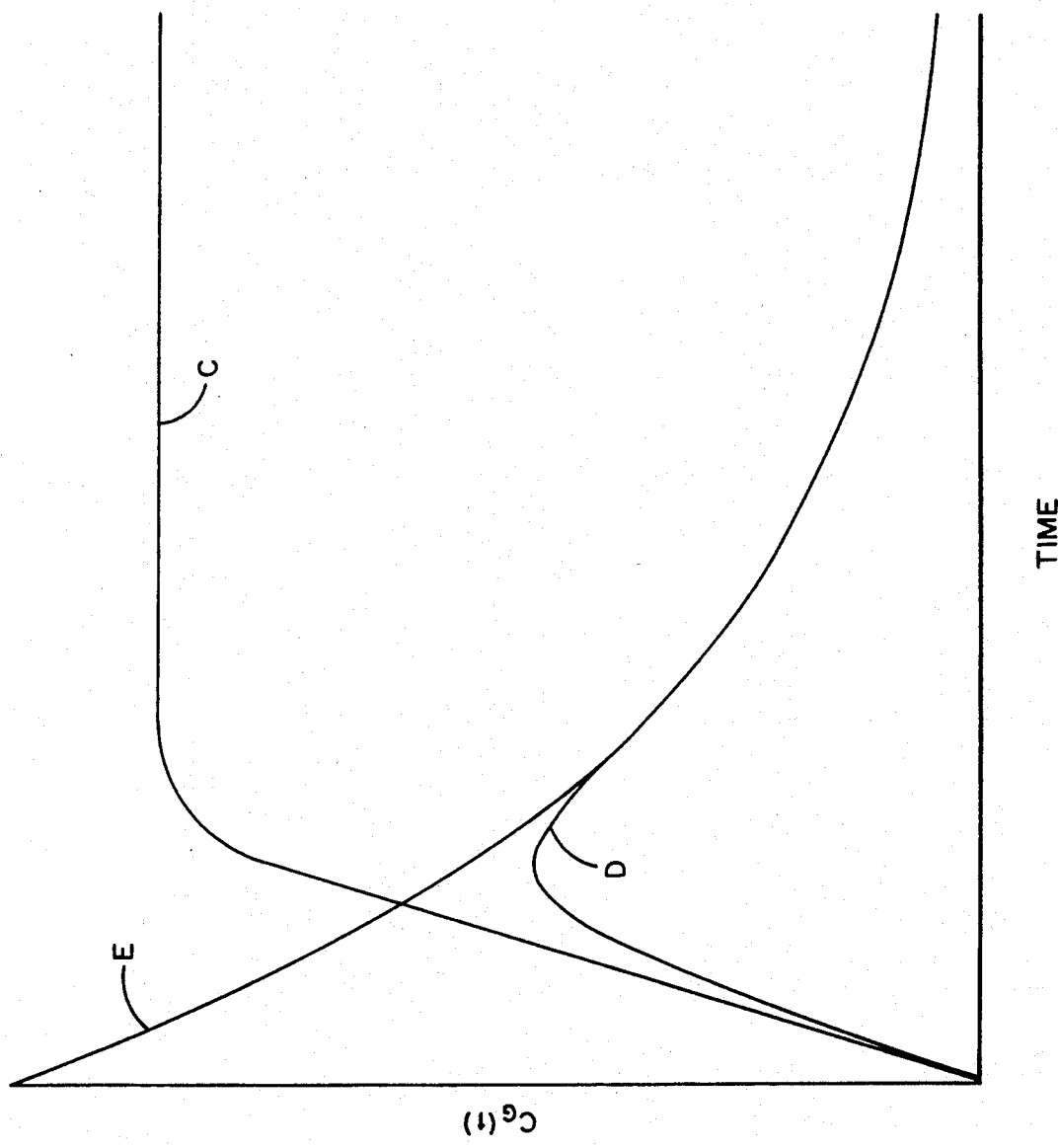
FIG. 5 is a graph showing the theoretical effects of the vapor concentration curves of variations in air volume and in solute solubility.
Figure 6:
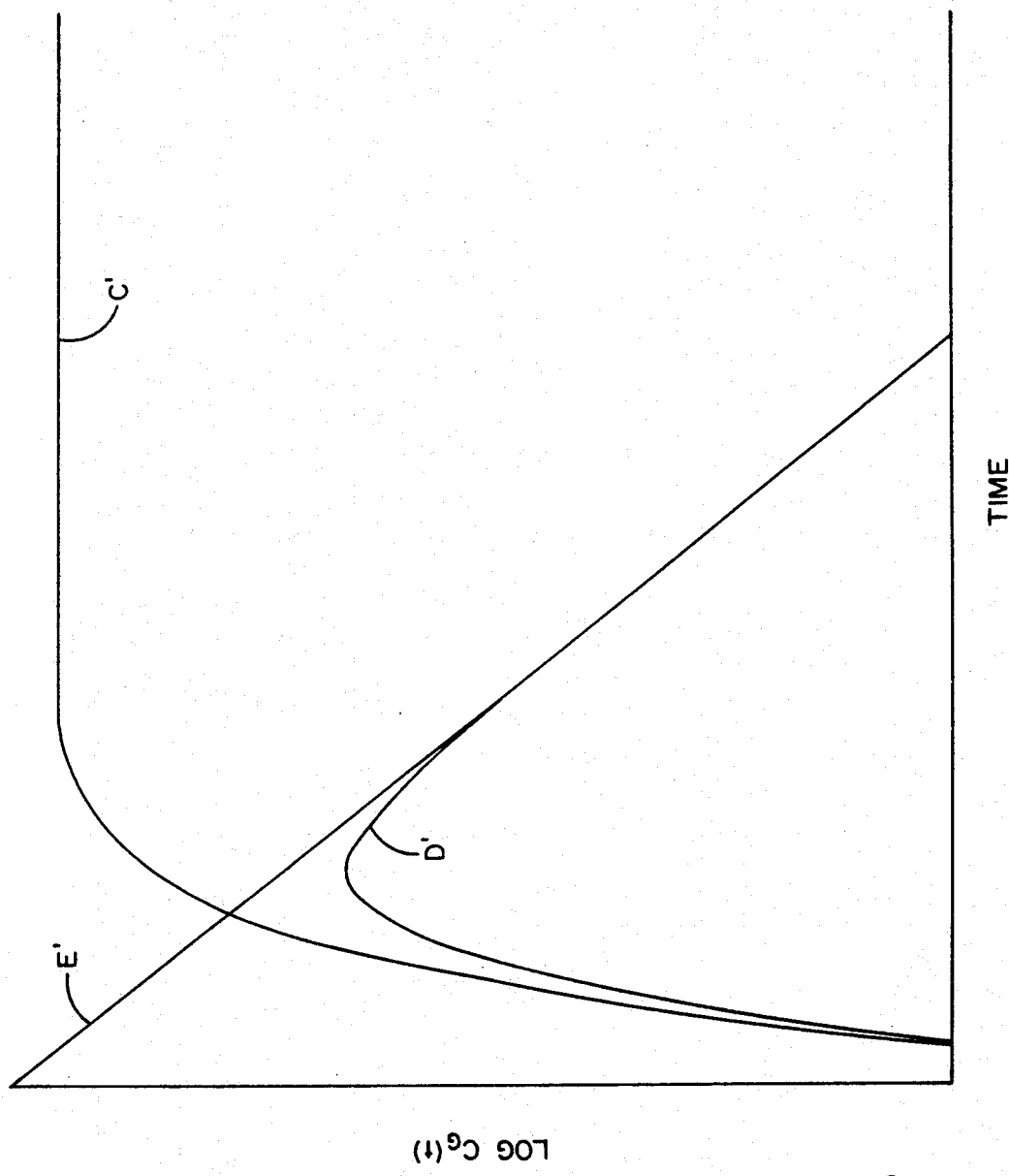
FIG. 6 is a graph based on FIG. 5, in which the data has been converted to logarithm values.

FIGS. 5 and 6 show curves which illustrate the effects of air volume variations and contaminant solubility variations. The X-axis represents time difference and the Y-axis represents vapor concentration difference. Curve C shows the effects of a substantial air volume combined with high solubility. Curve D shows the effects of substantial air volume combined with low solubility. Curve E shows the effects of negligible air volume combined with low solubility. The slopes C', D' and E' in FIG. 6 plot the logarithms of the curves in FIG. 5.

Multicomponent infrared analysis is only practical when there is a known set of no more than fifteen to twenty different substances that may be present. The calibration procedure, in general, involves obtaining a set of spectra of each of the pure substances individually, or of known combinations of them, and then using one of several different methods for selecting a set of infrared frequencies to use in determining the concentrations of the various substances in an unknown sample.

Since the user will know what substances are to be sought, the user has the opportunity to either look up or measure their solubilities and saturated concentrations. This will provide a rough estimate of what their depletion half volumes are likely to be. Alternatively, the user can measure the depletion half volumes of the pure substances by using the sparging IR system. This information will be quite useful in planning the measurement procedure for a given combination of pollutants.

A given measurement task is likely to involve substances having a very wide range of solubilities, from 1 (completely soluble) down to less than 0.001. In practice, the substances with the lower solubilities will be of the greatest concern. These may, in some cases, have half depletion volumes which are comparable to the air volume in the sparging IR system, thus making it highly desirable to use either the closed loop sparging system or the stopped flow approach disclosed in this application.

For a typical multiple component analysis, the procedure described below will allow the measurement of both the starting concentration and the partitioning function, K. During this procedure, it will be necessary for the computer to monitor the air flow rate at all times and to keep track of the times during which spectra are being gathered.

1. Start with the sparging vessel filled as high as practicable with a sample of the water to be analyzed.

2. Initiate air flow, with the flow rate set at a low enough value so that the rate of depletion for the most rapidly depleting solute is slow compared to the length of a period during which an individual spectrum is being gathered. If the depletion is too rapid, or if a long averaging time is needed in order to achieve adequate sensitivity, the air flow can be stopped during each gas cell measurement. During any non-flow period the depletion process will be stopped. Only the time intervals during which the air is flowing will be used in calculating P(O) and $P_o/S$. Continue this process until enough data is obtained to meet the requirements of the analysis for this first solute.

3. Simultaneously with step 2, the computer should be performing the various steps necessary to calculate the concentrations of the various substances, based on initial assumptions about solubility and saturated concentration. It should also start calculating the logarithms of the concentrations.

At this point, it would be a good idea to have a computer program operating to test the logarithm decay rate for the first substance analyzed. This should exhibit a rise time as the initial concentration passes through the gas cell, followed by a linear decay. If the decay is not linear, a more detailed analysis will be necessary.

4. Continue the above procedure until sufficient time history is obtained for each solute whose depletion rate is of the same order as either the rise time of the system or the measurement time per spectrum. At this point there should be enough data to determine $C_G(O)$ for each substance present. For the rapidly depleting solutes, it will be possible to extrapolate back to time zero. For the slowly depleting solutes, it will be possible to measure CG(O) directly.

There will also be enough information at this point to measure K for the rapidly depleting substances, by determining the slope of the logarithm depletion plot. To determine the value of this ratio for the other substances, proceed as follows.

5. Increase the air flow rate until the depletion rate of the next group of substances falls into the desirable range, and repeat the above procedure for these substances. In reducing the data, it will be necessary to keep track of the total volume of air flow from the beginning of the sparging process, in order to get an accurate measure of $C_G(O)$.

6. Step 5 can be repeated again with even higher air flow, if necessary, in order to analyze all of the solutes. If some of them have depletion rates which are too slow at even the highest practical air flow rates, the water volume can be reduced to increase the depletion rate. In doing this, care should be taken to keep the water deep enough so that the air becomes saturated with solute, in equilibrium with its concentration in solution, before the air reaches the surface. The required level can be determined by a separate set of experiments for each solute of interest.

Figure 7:
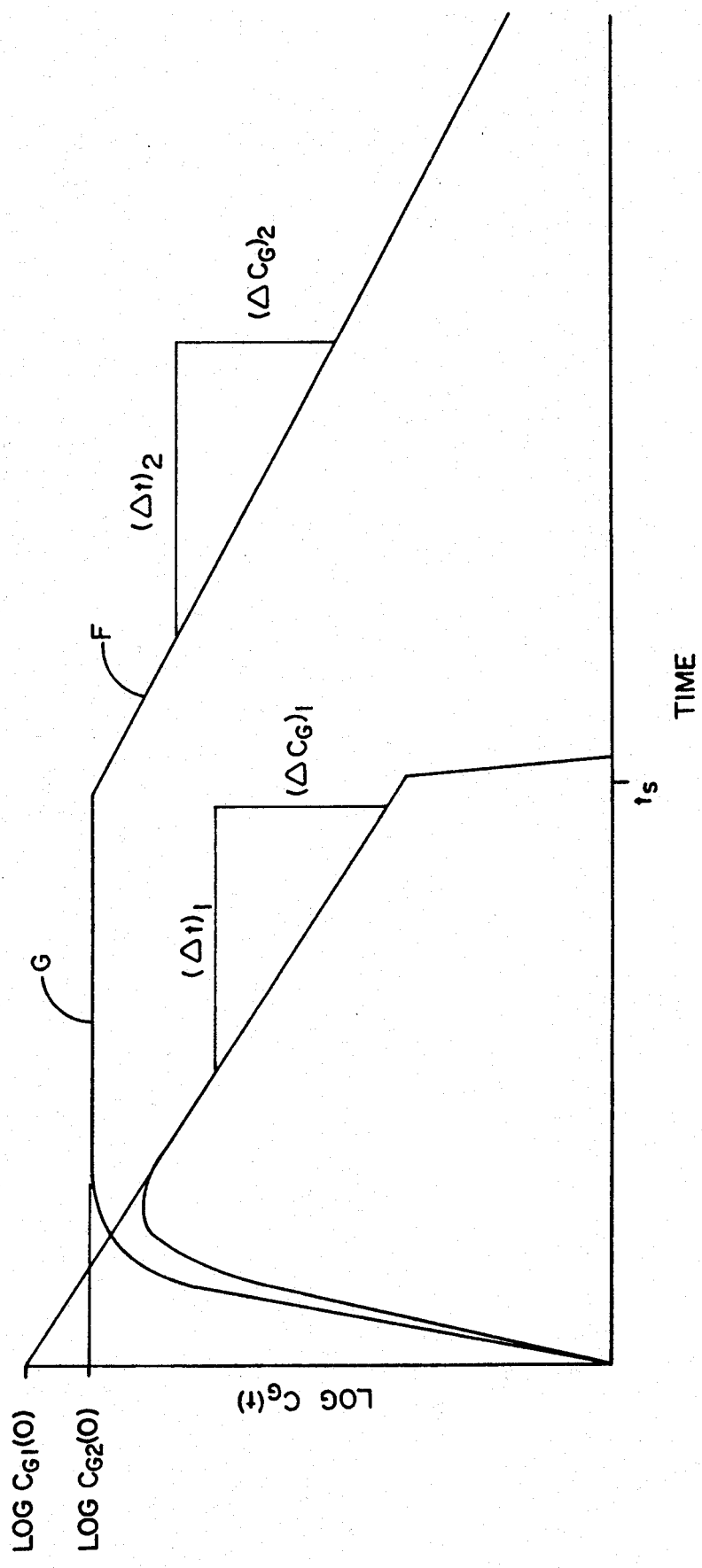
FIG. 7 is a graph showing the theoretical effect of an increase in flow rate at time $t_s$ on the vapor concentrations of two solutes having different depletion rates.

FIG. 7 illustrates the effect of increasing the air flow rate at time $t_s$ on the depletion rates of two solutes having different solubilities. The slopes of both curves should be measured during the initial slow flow period. The slope of the more slowly depleting solute should also be measured during the higher flow period. Its initial concentration can then be determined by extrapolating back along the two straight line segments, F and G.

The following explains the basis for certain assumptions in determining the half depletion volume:

Consider a closed vessel partially filled with polluted water. Designate the water volume and the air volume as $V_l$ and $V_g$, respectively. Both water molecules and solute molecules will start to evaporate into the air volume, and if enough time passes, they will reach equilibrium with their concentrations in the liquid mixture. In the case of water, the liquid concentration will usually be near 100%, so the concentration will be near the equilibrium value, $P_o$, of the pure substance, i.e., water in this case. In the case of a solute "s", the equilibrium value will be $$P = FP_o$$

where $P_o$ is used to designate the equilibrium concentration of a pure sample of this substance, and F is the fractional saturation, i.e., $F = C/S$, where C is the concentration by weight of the solute in the water, and S is the solubility. Combining these two expressions results in $$P = P_o C/S. \qquad (II-1)$$

Assume that the gas volume has been adjusted until, at equilibrium, exactly half of the solute has evaporated. In this case, the number of molecules of solute in the air will be equal to the number in the water. Call this adjusted volume the half depletion gas volume, $V_h$.

To determine the value of the half depletion volume, first consider the ideal gas law:

$$PV = nRT.$$

Here, P and V are concentration and volume, respectively, n is the number of moles of gas present, T is temperature (in degrees Kelvin) and R is a universal constant equal to 0.08206. At half depletion, the number of moles present in the gas phase (nG) is $$n_G = PV_h/RT. \qquad (II-2)$$

In the liquid phase, the number of moles ($n_L$) present is, by definition $$n_L = W/W_m$$

where W is the total weight of the solute present and $W_m$ is its molecular weight. However, the weight of the solute present is related to the weight of the water "$W_w$" by the concentration, i.e., $$W = CW_w.$$

Now, since the density of water is equal to 1, we have $W_w = V_w$, the water volume. And, since the pollutant concentrations are generally quite low, it is appropriate to make the approximation that the water volume is equal to the total liquid volume. Thus:

$$n_L = CV_w/W_m. \quad (\text{II-3})$$

Now, for the half depletion condition, $n_G = n_L$. Combining equations II-2 and II-3, yields $$V_h = CV_w RT/PW_m.$$

Combining this with equation II-1 results in $$V_h = V_w SRT/P_o W_m = V_w RT/W_m K. \quad (\text{I-4})$$

It is important to note that the solute concentration does not appear in this final equation. Thus, the half depletion volume will be the same no matter what the concentration is when the measurement starts. This condition leads directly to an exponential dependence of concentration on time.

Although the above expression was derived for a static equilibrium condition, it can be directly applied to the flowing gas case, provided the vapor concentration in each minute air bubble reaches equilibrium before the bubble reaches the surface of the water, and provided the liquid is continuously mixed, so that the solute concentration remains reasonably uniform. Although the sparging process will itself tend to mix the water, it may be necessary to introduce additional mixing, when analyzing rapidly depleting substances using the low air flow required in this case.

In this simplified description, the assumption has been made that the total air volume of the apparatus was small compared to the half depletion volume. This may not be the case for very low solubility solutes. Even in this case, however, the decay characteristic will be a simple exponential, which can be used to determine the initial concentration, and also the ratio of solubility to concentration.

Figure 8:
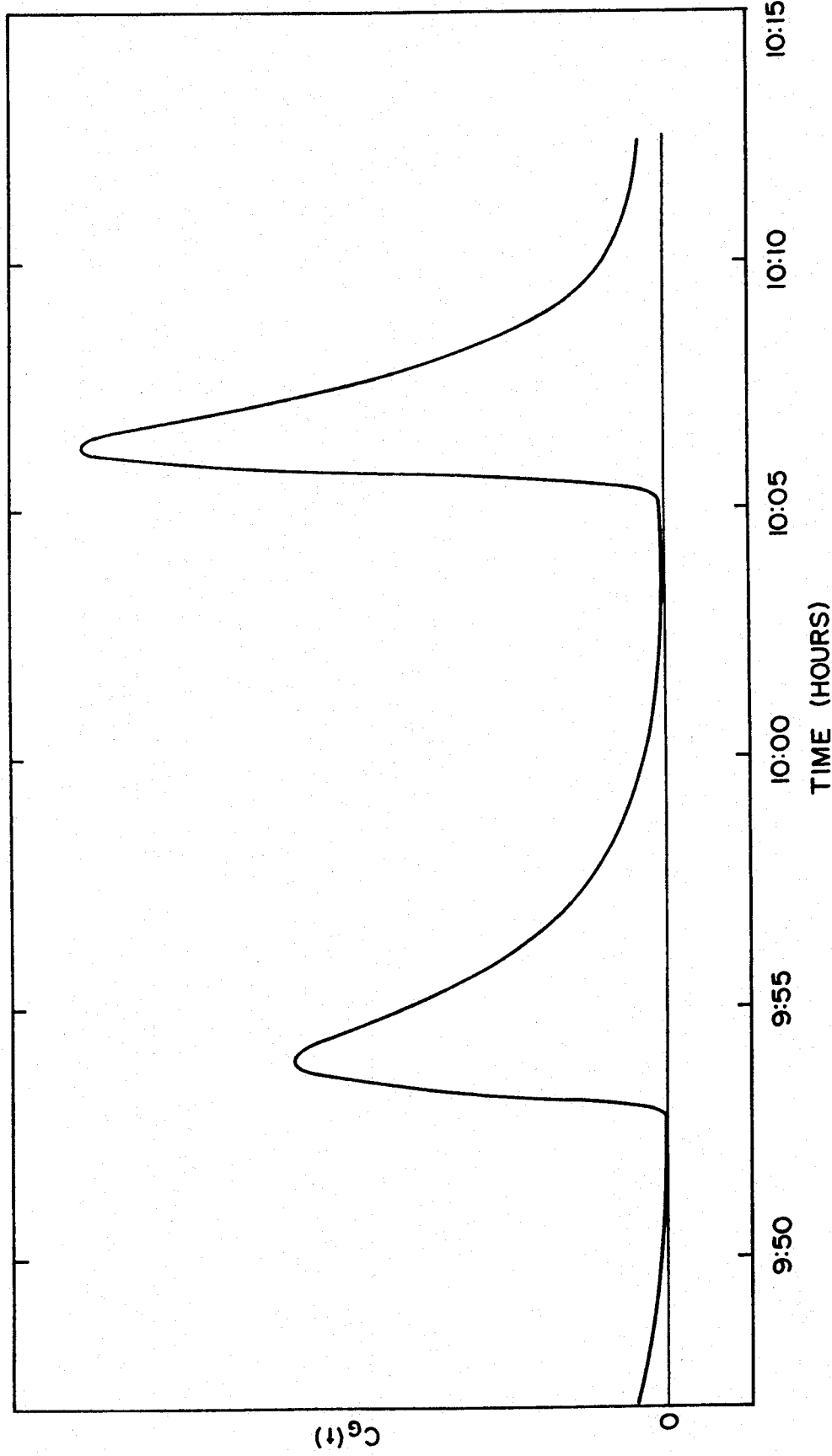
FIG. 8 is a sequence of two experimentally measured depletion curves corresponding to the same solute concentrations but different water temperatures.
Figure 9:
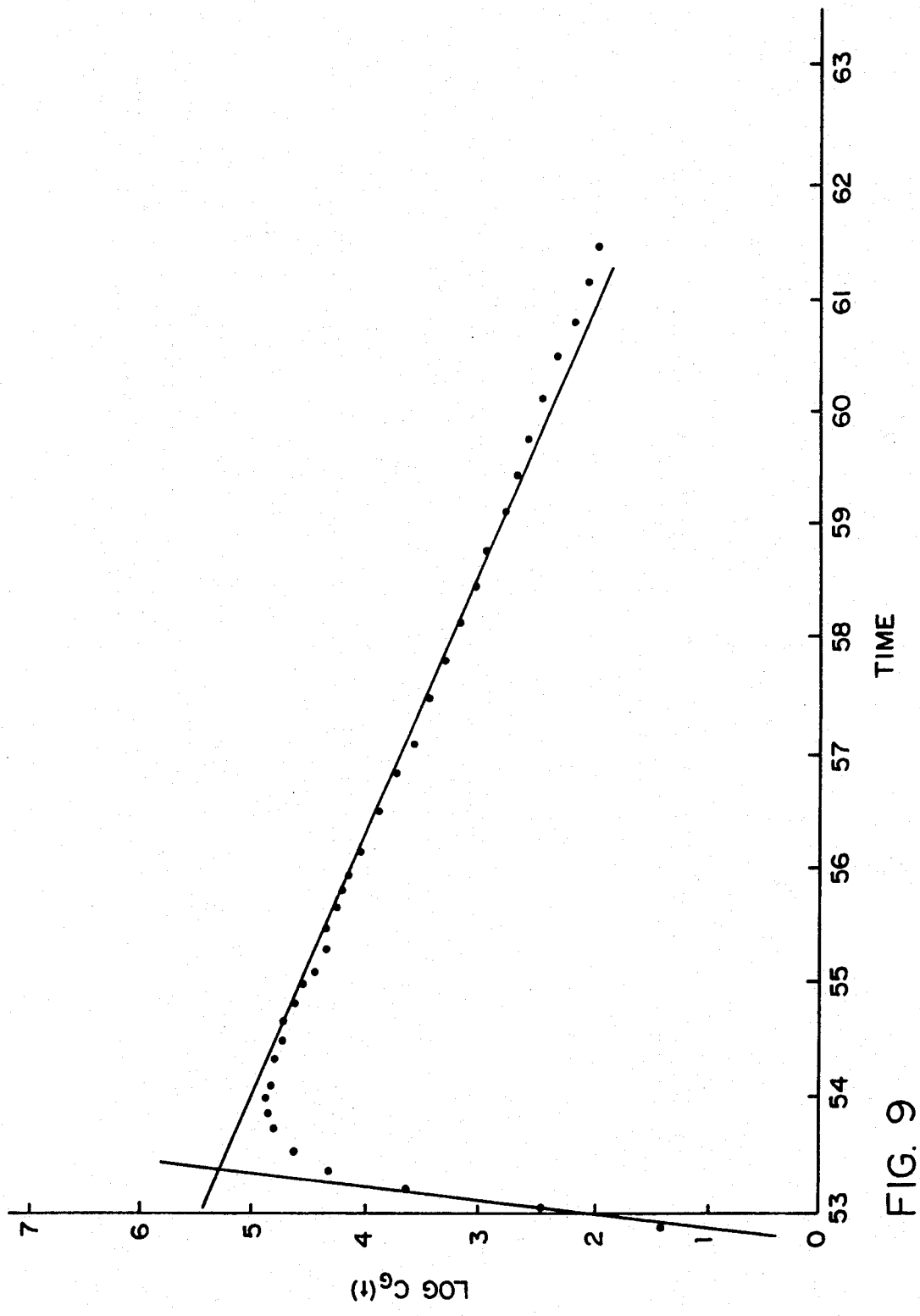
FIG. 9 is a logarithmic plot of the first depletion curve of FIG. 8.
Figure 10:
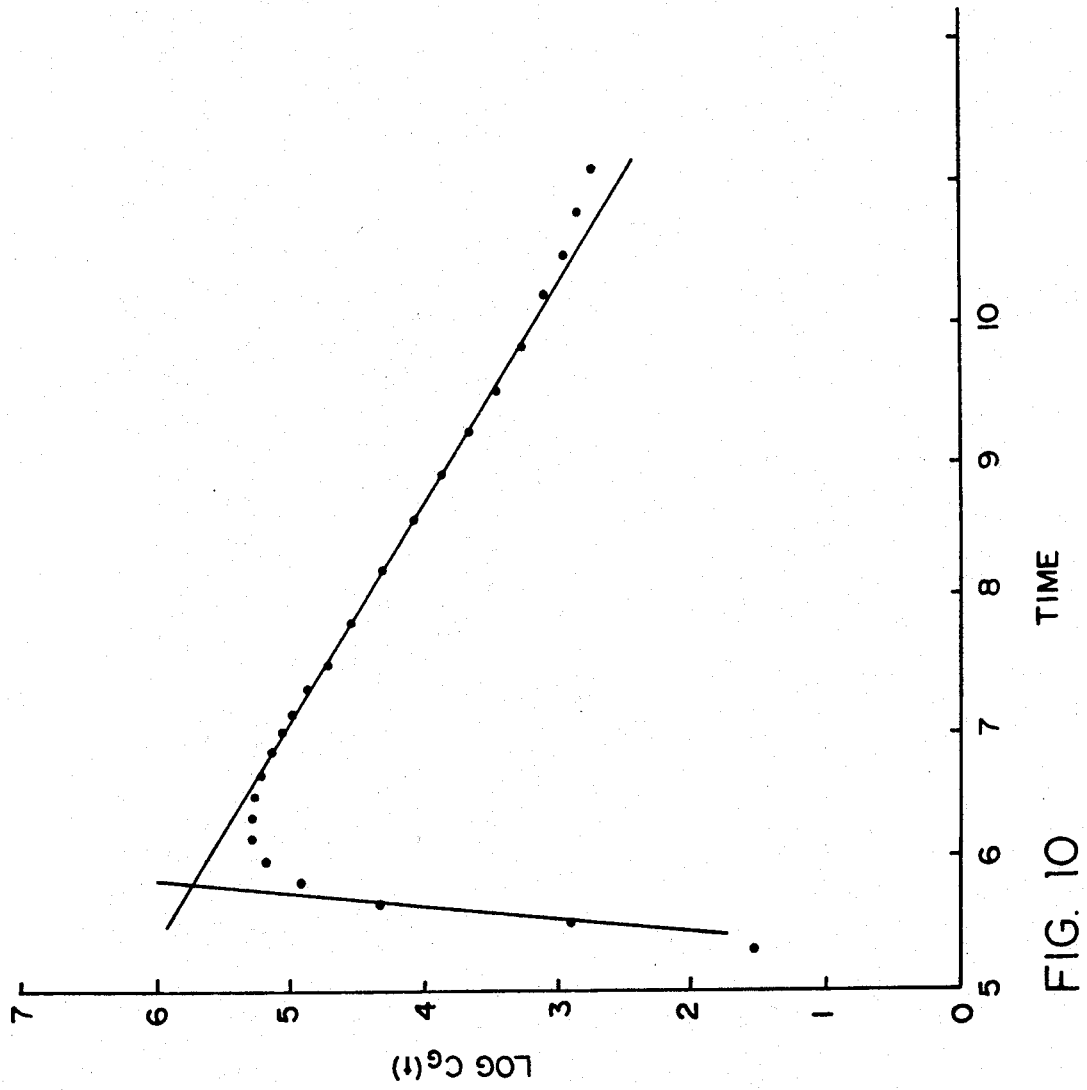
FIG. 10 is a logarithmic plot of the second depletion curve of FIG. 8.

FIGS. 8, 9, and 10 represent experimental data indicating the validity of the assumptions underlying the proposed method. FIG. 8 is a sequence of two measured depletion curves corresponding to a 20 part per million concentration of chloroform in water with water temperatures of 26 deg. C. and 39 deg. C. The substantial difference between the heights and widths of the two curves is largely due to the fact that the inherent concentration of the solute is much higher at the higher temperature.

FIG. 9 is a log plot of the first depletion curve of FIG. 8. The reasonable straight line fit to the log depletion curve confirms the assumption that the depletion would be exponential. Also, a straight line has been fitted to the rising edge of the curve. The fact that this edge is not vertical results from the finite air volume of the system. This, combined with the rounding of the peak, forces an assumption regarding the appropriate time to use as the starting time of the process. By a separate analysis, it has been determined that $t = 0$ should be set at the time when the leading edge of the sparged vapor reaches the mid point of the gas cell. To a first order approximation, this will correspond to the point where the two straight lines cross. This assumption has been used in analyzing the data.

The crossing point of FIG. 9 corresponds to log $C_G(O) = 5.3$, or $C_G(O) = 200$, in arbitrary units. The negative slope of the linear depletion curve is equal to $\alpha = 0.0073$ sec$^{-1}$. The predicted starting concentration in the solution will be proportional to $C_G(O)/\alpha = 2.74 \times 10^4$.

FIG. 10 is a log plot of the second depletion curve of FIG. 8. By the same procedure as used for FIG. 9, the following values have been arrived at: $\log C_G(O) = 5.74$; $C_G(O) = 311$; $\alpha = 0.0103$ sec$^{-1}$, and $C_G(O)/\alpha = 3.03 \times 10^4$.

Comparing the above two results, it is found that the increase in temperature between the two samples led to a 55% increase in the initial concentration, but only a 10% increase in the predicted liquid concentration. This is probably within the experimental error for this measurement.

From the foregoing description, it will be apparent that the method disclosed in this application will provide the significant functional benefits summarized in the introductory portion of the specification.

The following claims are intended not only to cover the specific embodiments disclosed, but also to cover the inventive concepts explained herein with the maximum breadth and comprehensiveness permitted by the prior art.

What is claimed is:

1. A method for determining the concentration of a subject solute in a volume of liquid, which comprises:
   providing in a container a volume of liquid including a subject solute whose concentration is to be measured;
   flowing a gas through the liquid for the purpose of removing a vaporized sample containing the subject solute;
   directing the vaporized sample to an analytical instrument capable of measuring gas concentration as a function of time;
   measuring the flow rate of the gas;
   obtaining data proportional to the concentration of the gas as a function of time, such data being measured by means of the analytical instrument;
   recording said data at a plurality of spaced points in time, some of which points are sufficiently spaced from the starting time to occur when the concentration of the subject solute is not rising; and
   extrapolating, from the concentration data at said plurality of spaced points in time, the value of the vapor concentration of the subject solute which would have existed at point zero except for the initial rising period of concentration.

2. The method of claim 1 in which the measurement is accomplished by an infrared spectrometer, used in conjunction with a gas cell.

3. The method of claim 2 which also comprises:
   causing the vapor phase of the subject solute to be substantially in equilibrium with its liquid phase.

4. The method of claim 2 which also comprises:
   converting the time-spaced recorded gas cell data into a logarithmic slope preparatory to extrapolating back to time zero to determine the initial vapor concentration of the subject solute.

5. The method of claim 4 in which the steps of the method are performed to determine the time zero vapor concentrations of a plurality of subject solutes.

6. The method of claim 2 in which the steps of the method are performed to determine the time zero vapor pressures of a plurality of subject solutes.

7. The method of claim 2 which also comprises:

fitting the depletion curve to an exponential form so as to determine a depletion rate constant.

8. The method of claim 7 which also comprises:
using the depletion rate constant, in conjunction with the measured flow rate and water volume, to determine the ratio of inherent vapor pressure to solubility for solute.

9. The method of claim 7 which also comprises:
determining the concentration of the solute in solution directly from the measured initial vapor concentration and the vapor pressure to solubility ratio.

10. The method of claim 9 in which the steps of the method are performed to determine the concentrations of a plurality of subject solutes.

11. The method of claim 8 in which the steps of the method are performed to determine the vapor pressure to solubility ratios of a plurality of subject solutes.

12. The method of claim 1 which also comprises:
causing the vapor phase of the subject solute to be substantially in equilibrium with its liquid phase.

13. The method of claim 1 which also comprises:
converting the time-spaced recorded gas cell data into a logarithmic slope preparatory to extrapolating back to time zero to determine the initial concentration of the subject solute.

14. The method of claim 13 in which the steps of the method are performed to determine the time zero vapor concentrations of a plurality of subject solutes.

15. The method of claim 1 in which the steps of the method are performed to determine the time zero vapor concentrations of a plurality of subject solutes.

16. The method of claim 1 in which also comprises:
fitting the depletion curve to an exponential form so as to determine a depletion rate constant.

17. The method of claim 16 which also comprises:
using the depletion rate constant, in conjunction with the measured flow rate and water volume, to determine the ratio of inherent vapor pressure to solubility for the solute.

18. The method of claim 16 which also comprises:
determining the concentration of the solute in solution directly from the measured initial vapor concentration and the vapor pressure to solubility ratio.

19. The method of claim 18 in which the steps of the method are performed to determined the concentrations of a plurality of subject solutes.

20. The method of claim 17 in which the steps of the method are performed to determine the vapor pressure to solubility ratios of a plurality of subject solutes.

21. A method of determining the concentration of a subject solute in a volume of liquid, which comprises:
providing in a container a volume of liquid including a subject solute whose concentration is to be measured;
flowing a gas through the liquid for the purpose of removing a vaporized sample containing the subject solute, thereby causing controlled depletion of the solute;
directing the vaporized sample to an analytical instrument capable of measuring gas concentration as a function of time;
measuring the flow rate of the gas;
obtaining data proportional to the concentration of the gas as a function of time, such data being measured by means of the analytical instrument;
recording said data at a plurality of spaced points in time, some of which points are sufficiently spaced from the starting time to occur when the concentration of the subject solute is not rising; and
using the recorded time dependent concentration data to determine the initial concentration of solute in the liquid volume.

22. The method of claim 21 in which the concentration of solute is assumed to follow an exponential time dependence.

23. The method of claim 21 in which the initial liquid solute concentration is assumed to be proportional to the area under the depletion curve.

24. The method of claim 23 in which the area under the depletion curve is determined by first fitting an exponential function to the recorded date.

25. The method of claim 23 in which the measurement is accomplished by an infrared spectrometer, used in conjunction with a gas cell.

26. The method of claim 23 which also comprises:
causing the vapor phase of the subject solute to be substantially in equilibrium with its liquid phase.

27. The method of claim 23 in which the steps of the method are performed to determine the time zero vapor concentrations of a plurality of subject solutes.

* * * * *